(12) United States Patent
Greenwald (10) Patent No.: US 8,538,705 B2
(45) Date of Patent: Sep. 17, 2013

(54) SYSTEM AND METHOD OF ASSESSING ANALGESIC ADEQUACY USING BIOPOTENTIAL VARIABILITY

(75) Inventor: Scott D. Greenwald, Medfield, MA (US)

(73) Assignee: Covidien LP, Mansfield, MA (US)

( * ) Notice: Subject to any disclaimer, the term of this patent is extended or adjusted under 35 U.S.C. 154(b) by 15 days.

(21) Appl. No.: 13/159,459

(22) Filed: Jun. 14, 2011

(65) Prior Publication Data
US 2011/0245709 A1    Oct. 6, 2011

Related U.S. Application Data

(63) Continuation of application No. 11/731,510, filed on Mar. 30, 2007, now abandoned.

(60) Provisional application No. 60/787,992, filed on Mar. 31, 2006.

(51) Int. Cl.
*G01N 33/48* (2006.01)
*A61B 5/0488* (2006.01)

(52) U.S. Cl.
USPC ........................................... 702/19; 600/544

(58) Field of Classification Search
None
See application file for complete search history.

(56) References Cited

U.S. PATENT DOCUMENTS

| | | | |
|---|---|---|---|
| 5,458,117 A | 10/1995 | Chamoun et al. | |
| 5,601,090 A | 2/1997 | Musha | |
| 6,117,075 A | 9/2000 | Barnea | |
| 6,654,632 B2 | 11/2003 | Lange et al. | |
| 6,731,975 B1 | 5/2004 | Viertio-Oja et al. | |
| 6,751,499 B2 | 6/2004 | Lange et al. | |
| 6,757,558 B2 | 6/2004 | Lange et al. | |
| 6,801,803 B2 | 10/2004 | Viertio-Oja | |
| 6,826,426 B2 | 11/2004 | Lange et al. | |
| 6,934,579 B2 | 8/2005 | Mantzaridis et al. | |
| 7,215,994 B2 | 5/2007 | Huiku | |
| 7,367,949 B2 | 5/2008 | Korhonen et al. | |
| 2006/0004296 A1 | 1/2006 | Huiku et al. | |
| 2006/0217628 A1 | 9/2006 | Huiku | |
| 2007/0167694 A1 | 7/2007 | Causevic et al. | |
| 2008/0167540 A1 | 7/2008 | Korhonen et al. | |

FOREIGN PATENT DOCUMENTS

| | | |
|---|---|---|
| JP | 03136408 A | 6/1991 |
| WO | 03084396 | 10/2003 |
| WO | 2004105601 | 12/2004 |

OTHER PUBLICATIONS

Mattews et al. Anest. Analg. 2003;96:1062-4.*
Bloom, M., et al., "Analgesics Decrease Arousal Response to Stimulation as Measured by Changes in Bispectral Index (BIS)," Anesthesiology 1996; 85(3A):A481.
Bloom,. M. et al., "BIS Variability Reflects Analgesia," J. Neurosurg. Anesthesiol. 2005; 17(4): 254-5.
Duggleby, W., et al., "Cognitive Status and Postoperative Pain: Older Adults," J. Pain. Symptom Manage 1994; 9:19-27.
Gan TJ. et al., "Bispectral Index Monitoring Allows Faster Emergence and Improved Recovery From Propofol, Alfentanil, and Nitrous Oxide Anesthesia," Anesthesiology 1997; 8494): 808-15.
Guignard B. et al., "The Effect of Remifentanil on the Bispectral Index Change and Hemodynamic Responses After Orotracheal Intubation," Anesth. Analg. 2000; 90(1): 161-7.
Iselin-chaves IA et al., "The Effect of the Interaction of Propofol and Alfentanil on Recall, Loss of Consciousness, and the Bispectral Index," Anesth. Analg. 1998; 87(4):949-55.
Jopling MW. et al., "Changes in Bispectral Index (BIS) in the Presence of Surgical Stimulation Reflect the Level of Analgesia," Anesthesiology 1996; 85(3A); A478.
Kreuer, et al., "Comparison of Alaris AEP Index and Bispectral Index During Propofol-Remifentanil Anaesthesia," British Journal of Anaesthesia 91 (3): 336-340, 2003.
Lynch, EPMD., et al. "The Impact of Postoperative Pain on the Development of Postoperative Delirium," Anest. & Analg. 1998; 86(4):781-5.
Monk TG, et al., "Anesthetic Management and One-Year Mortality After Noncardiac Surgery," Anesth. Analg. 2005; 100:4-10.
Morrison, RS, et al., "Relationship Between Pain and Opioid Analgesics on the Development of Delirium Following Hip Fracture," J. Gerontol. A. Biol. Sci. Med. Sci. 2003; 58:76-81.
Paravicini, et all., "Medline on STN," Database Medline, DN PubMed ID: 3919607 (Der Anaesthesist, (Jan. 1985 ) vol. 34, No. 1, pp. 20-27).
Schneider, et al., "Quality of Perioperative AEP-Variability of Expert Ratings," British Journal of Anaesthesia, 91 (6), 905-8 (2003).
Xie Z., et al., "The Inhalation Anesthetic Isoflurane Induces a Vicious Cycle of Apoptosis and Amyloid β-Protein Accumulations," J. Neurosci. 2007; 27:12-1254.
International Search Report, mailed on Feb. 29, 2008 for Application No. PCT/US 07/65708, p. 1.
Written Opinion of the International Searching Authority, mailed on Feb. 29, 2008 for Application No. PCT/US 07/065708, pp. 1-4.

* cited by examiner

*Primary Examiner* — Michael Borin (57) ABSTRACT

The system and method for predicting and measuring a subject's analgesic state and analgesic adequacy. Biopotential signals are obtained from a subject through electrodes. A processor will compute a measure that is representative of the subject's sedative state and/or muscle activity. A metric representative of such measures is then determined. In the case where a measure is taken of both the subject's sedative state and muscle activity the two measures are combined into an index representative of the subject's analgesic state and analgesic adequacy.

20 Claims, 8 Drawing Sheets

FIG. 4C

SYSTEM AND METHOD OF ASSESSING ANALGESIC ADEQUACY USING BIOPOTENTIAL VARIABILITY

CROSS REFERENCE TO RELATED APPLICATION

This application is a continuation of U.S. patent application Ser. No. 11/731,510, filed on Mar. 30, 2007, which is incorporated herein by reference in its entirety for all purposes.

FIELD OF THE INVENTION

The field of the present invention relates to medical monitoring tools, and more particularly, to a system and method for predicting and measuring a subject's analgesic state and analgesic adequacy.

BACKGROUND OF THE INVENTION

A patient undergoing anesthesia for a surgical procedure generally receives one or more pharmacological anesthetic agents. Different anesthetic agents produce different effects, the most important of which are sedation or hypnosis (the lack of consciousness or awareness of the surrounding world), analgesia (the blunting or absence of pain) and paralysis (lack of movement). Anesthetic agents may provide one or more of these effects and to varying extents. For example, neuromuscular blocking agents provide potent paralysis, but no sedation or analgesia. Opioids provide analgesia and relatively light levels of sedation. Volatile anesthetic agents provide significant levels of sedation and much smaller levels of analgesia, while the intravenous sedative agent propofol provides sedation but essentially no analgesia. For this reason, anesthesia providers generally administer several of these agents simultaneously to provide the desired set of effects. For example, an anesthesia provider may administer a volatile anesthetic agent for its sedative effect, a neuromuscular blocking agent for paralysis and an opioid agent to provide analgesia. In general, the magnitude of the effects provided by these agents are dose-dependent; the higher the dose, the more profound the effect.

The anesthetic administration is complicated by the multiple effects of the administered anesthetic agents. For example, since volatile agents have analgesic as well as sedative effects, an increase in the administered concentration of a volatile agent will result in a concomitant, and possibly undesired, increase in analgesic effect. All anesthetic agents have deleterious effects associated with excessive doses. While the effect on the patient may be estimated from the administered dose, patients vary widely in their response to a specific dose and such estimates are therefore based upon group norms (average effects). While the group norm may be representative of the effect of a specific dose on a population of patients, the actual effect in any one patient may vary widely.

It would therefore be beneficial to the patient to monitor the effect of the administered anesthetic agents to ensure that the patient receives the appropriate dose of anesthetic agents. It is common in anesthesia practice to monitor the sedative effects of anesthetic agents by the use of devices which analyze the patient's electroencephalograph (EEG). One such device is the line of monitors made by Aspect Medical Systems, Inc. (Norwood, Mass.) which calculate the Bispectral Index®. By way of example, U.S. Pat. No. 5,458,117, entitled CEREBRAL BIOPOTENTIAL ANALYSIS SYSTEM AND METHOD, issued to Chamoun et al. on Oct. 17, 1996, which is assigned to the assignee of the present invention, describes a system and method for generating a bispectral index from EEG signals. The Bispectral Index® (BIS®) discussed in that patent is an electroencephalograph (EEG)-based measure which quantifies a patient's level of consciousness during anesthesia and sedation from EEG signals acquired from scalp, forehead or temple electrodes. BIS is a single time varying number that is generally indicative of a patient's sedative state and is scaled from 0 to 100, where 100 is fully awake and alert and zero represents isoelectric EEG activity. BIS may be used by anesthesia providers to effectively monitor the sedative state of a patient during a surgical procedure and to maintain a patient's sedative or hypnotic state in an optimal range, generally 50-60.

Similarly, a patient's level of paralysis may be measured by a tetanic nerve simulator, a device which delivers a train of four electrical stimuli to the nerve in the forearm innervating the muscles of the thumb. Each electrical stimulus results in a twitch of the patient's thumb, which may be quantified using a strain gauge attached to the patient's thumb. Successively higher levels of paralysis result in the abolition of the twitch responses, beginning with the fourth and final response and finally abolishing the first twitch response. The degree of paralysis may be gauged by the degree to which the twitches are abolished. It is common practice to administer neuromuscular blocking agents until three of the four twitches are abolished.

While BIS may be used to monitor a patient's level of sedation and a tetanic nerve simulator used to monitor the degree of paralysis, there is no similar measure of analgesia. Typically, the adequacy of analgesia is gauged by the presence or absence of various indirect autonomic signs, such as hemodynamic responses (hypertension or tachycardia), sweating, eye tearing or movement. These measures are non-specific, however, and a patient may experience significant pain without exhibiting any of them. In addition, agents administered to maintain blood pressure and heart rate within desired ranges may abolish hemodynamic responses.

Pain is a subjective, self-reported phenomenon. It is often associated with somatic responses, such as sweating, movement, etc. The measurement of pain is difficult, since patient descriptions vary. Standardized measurement techniques such as Visual-Analog Scales (VAS), which ask a patient to rank their pain on a numeric scale (e.g., 0-10), provide some degree of comparability. However, since different patients have different pain thresholds and expectations, VAS assessments are inherently limited. In addition, VAS assessments are not useful when a patient cannot respond, such as during surgery. Postoperative pain and lower doses of opioids have been determined to be risk factors for increased risk of postoperative delirium, with the conclusion that more effective control of postoperative pain improves outcomes by reducing the incidence of postoperative delirium [Lynch EPMD, Lazor MAMD, Gellis JEMD, et al. The Impact of Postoperative Pain on the Development of Postoperative Delirium. Anesthesia & Analgesia 1998; 86(4):781-5; Morrison R S, Magaziner J, Gilbert M et al. Relationship between Pain and Opioid Analgesics on the Development of Delirium Following Hip Fracture. J Gerontol A Biol Sci Med Sci 2003; 58: 76-81]. Perioperative pain is also linked to postoperative cognitive dysfunction (POCD). Duggleby determined that postoperative pain, not analgesic intake, predicted postoperative mental status decline, and recommended improved pain management [Duggleby W, Lander J. Cognitive Status and Postoperative Pain: Older Adults. J Pain Symptom Manage 1994;

9:19-27]. Minimization of intraoperative and postoperative pain should therefore result in improved patient outcomes.

As discussed earlier, volatile anesthetics have both sedative (hypnotic) and analgesic properties, and are often administered at quite large concentrations in order to assure adequate analgesia and hemodynamic stability, especially if relatively small doses of opioids and other analgesics are in use. Volatile anesthetics have recently been associated with processes leading to cell death and amyloid β-protein aggregation; excessive aggregation of amyloid β-protein is the hallmark of Alzheimer's disease [Xie Z, Dong Y, Maeda U, et al. The Inhalation Anesthetic Isoflurane Induces a Vicious Cycle of Apoptosis and Amyloid β-Protein Accumulation. J. Neurosci. 2007; 27:12-1254]. In addition, deeper anesthetic intraoperative hypnotic levels have been linked with increased rates of postoperative mortality [Monk T G, Saini V, Weldon B C, Sigl J C: Anesthetic Management and One-Year Mortality after Noncardiac Surgery. Anesth Analg 2005; 100:4-10].

While excessive doses of the various anesthetic agents may have deleterious effects, inadequate doses may result in different but also undesirable effects. It is therefore important that all the pharmacological components of an anesthetic (sedative/hypnotic, analgesic, paralytic, etc.) be properly administered and titrated to the patient's requirement. While monitoring means exist to determine the adequacy of the sedative/hypnotic and paralytic states, no similar monitoring technology allows the objective assessment of analgesic state and analgesic adequacy. A patient's analgesic state is the degree of analgesia provided by the administered pharmacological agents, while the analgesic adequacy is the degree to which the current level of analgesia is sufficient to block the current and expected level of noxious stimuli. The ability to assess analgesic state and determine analgesic adequacy during surgery and anesthesia would be extremely useful to establish the analgesic dose required and would improve outcome over existing practice.

U.S. Pat. No. 5,601,090 issued to Musha discloses an apparatus and method for determining the somatic state of a human subject. The method acquires characteristic values of the subject, which may be brain waves, muscle potentials, heart-rate, eye-movement and frequency of eye blinks, or any combination thereof. A neural network model is applied to these characteristic values to determine the subject's somatic state, which Musha defines as mental state due to such things as the subject's emotions (e.g., joy, anger, happiness, sadness, elation, surprise, disgust or fear), level of mental activity (e.g., as a result of doing mental arithmetic or writing a poem) or motor activity (e.g., moving a hand or foot). The Musha patent does not quantify the subject's analgesic state or adequacy, or any state related to the effect of medications.

U.S. Pat. Nos. 6,654,632; 6,751,499; 6,757,558 and 6,826,426 issued to Lange et al. disclose an objective pain measurement system and method based on bilateral biopotentials recorded from electrodes placed symmetrically about the midline on the forehead of a subject. The Lange et al. patents teach that in general, biopotentials on the subject's skin surface are generated by several sources, including background electroencephalographic (EEG) activity, electrodermal activity, electromyographic (EMG) activity, motion artifacts (such as caused by eyeball, eyelid and head movements), and other electrophysiological phenomena. Background EEG measurements from each side of the vertical midline and artifacts, such as those caused by eyeball movement, are negatively-correlated while pain signals from each side of the vertical midline are generally positively correlated and may override the negatively correlated EEG activity. Consequently, the system and method of pain detection of the Lange et al. patents preferably use positive bilateral correlation as a discriminant for pain signals when the measurements are taken from electrodes located on opposite sides of the subject's vertical midline. The Lange et al. patents further state that pain detection may also use signal linearity to distinguish pain, because pain signals detected from each side of the vertical midline are generally linearly related. In contrast, various artifacts in the detected signal, even those that are positively correlated (e.g., eyelid or head movements), are often not linearly related. The Lange et al. patents teach the use of coherence to determine whether the bilateral signals are linearly related. The Lange et al. patents further teach that signals between about 0.5 Hertz and about 2 Hertz appear to carry the bulk of pain intensity information. The system and method described in the Lange et al. patent computes a quantified pain level signal using band pass filtering to 0.1 to 2 Hz, linear prediction, frequency transformation, non-linear weighted averaging of the frequency-transformed signal components and scaling of the weighted average. The Lange et al. patents do not discuss the source of the pain signals, nor why these signals are positively correlated while the non pain-related signals are not or why pain signals detected from each side of the vertical midline are generally linearly related while non-pain signals from each side of the vertical midline are not linearly related. The Lange et al. patents teach a system and method for measuring pain and for differentiating pain signals from artifact. However, they do not teach a method of determining analgesic state or analgesic adequacy, nor do they teach how to resolve the separate influences of the level of consciousness and pain on the EEG signal.

Shander evaluated a measure called FACE based on the ratio of EMG activity in four facial muscles and determined that the time in minutes of the FACE RATIO>20 during surgery was associated with total amount of administered postoperative analgesics [Shander A, Qin F, Bennett H. Prediction of Postoperative Analgesic Requirements by Facial Electromyography during Simultaneous BIS Monitoring. European Journal of Anaesth 2001; 18 (Suppl. 21):A464].

U.S. Pat. No. 6,731,975 issued to Viertiö-Oja, et al, teach a method and apparatus for ascertaining the cerebral state of a patient, specifically for ascertaining the depth of anesthesia of the patient. The entropy of the patient's EEG signal data is determined as an indication of the cerebral state. A frequency domain power spectrum quantity is obtained from the patient's EMG signal data. The EEG entropy indication and the EMG power spectrum indication are combined into a composite indicator that provides an immediate indication of changes in the cerebral state of the patient. In an alternate embodiment, the frequency range over which the entropy of the biopotential signal from the patient is determined is broadened to encompass both EEG signal data and EMG signal data and the entropy so determined used as an indication of the patient's cerebral state. In a continuation patent U.S. Pat. No. 6,801,803, Viertiö-Oja et al. teach the use of time windows of differing lengths. For lower frequency component, longer time windows are used. For higher frequency components, shorter time windows are used. Such techniques are common in the art of wavelet analysis. Both of these patents teach the combination of a power spectral measure from the EMG with an entropy measure derived from the EEG in order to ascertain the depth of anesthesia of the patient with a faster response time over the EEG metric alone. Neither of the Viertiö-Oja et al. patents teach the determination of the analgesic state or analgesic adequacy of a patient.

Bloom et al. [Bloom M, Greenwald S D, Day R, Analgesics Decrease Arousal Response to Stimulation as Measured by Changes in Bispectral Index (BIS). Anesthesiology 1996; 85(3A):A481] investigated the intrinsic variability of BIS in volunteers who received various concentrations of sedative and analgesic agents. Bloom determined that the variability in the absence of stimulation was decreased by the addition of analgesic agents compared to sedative agents alone. Bloom and Jopling (Jopling M W, Cork R, Greenwald S D. Changes in the Bispectral Index (BIS) in the Presence of Surgical Stimulation Reflect the Level of Analgesia. Anesthesiology 1996; 85 (3A): A478) reported that analgesics blunt the increase in BIS that follows surgical stimulation. In a study evaluating the response to painful stimulus, Iselin-Chaves demonstrated that the absolute change in BIS after a painful stimulus was significantly decreased by both an increase in the concentration of the sedative agent and the presence of the analgesic agent, [Iselin-Chaves I A, Flaishon R, Sebel P S, et al. The Effect of the Interaction of Propofol and Alfentanil on Recall, Loss of Consciousness, and the Bispectral Index. Anesth Analg 1998; 87(4):949-55]. Guignard also investigated the effect of the addition of an analgesic agent of the sedative in terms of response of BIS to the stimulus of intubation. His group concluded that "the addition of an analgesic (remifentanil) to propofol (a sedative) affects BIS only when a painful stimulus is applied. Moreover, remifentanil attenuated or abolished increases in BIS and MAP (mean arterial pressure) in a comparable dose-dependent fashion" [Guignard B, Menigaux C, Dupont X, et al. The Effect of Remifentanil on the Bispectral Index Change and Hemodynamic Responses after Orotracheal Intubation. Anesth Analg 2000; 90(1):161-7]. In a later publication Bloom suggested that using a variability measure based on BIS (the maximum minus the minimum BIS value over a three minute time window), wide short-term BIS variability may be an indicator of insufficient analgesia [Bloom M, Jurmann A, Cuff G, Bekker A. BIS Variability Reflects Analgesia. J Neurosurg Anesthesiol 2005; 17(4):254-5].

U.S. patent application Ser. No. 11/211,137 filed by Viertiö-Oja, et al. teaches a method and apparatus for measuring the responsiveness of a subject with a lowered level of consciousness. In the system of the Viertiö-Oja et al. application, the EEG signal measured from a patient is digitized, filtered to exclude high- and low-frequency artifacts and processed as sets of 5 second time windows or "epochs". The processing method calculates the high-frequency power of the EEG signal, which the Viertiö-Oja et al. application defines as the power in a band extending from 20 Hz to 35 Hz within a single epoch, and stores the calculated value. This calculation is repeated for each epoch producing a time series (known as the first measure), which is the high-frequency EEG power in each epoch.

The processing method of the Viertiö-Oja et al, application next calculates a change variable indicative of the changes in the high-frequency EEG power. The process first finds the minimum value within the preceding 1 minute of the first measure. The change variable is then determined by subtracting the minimum value of the first measure from the current value of the first measure. Finally, a responsiveness index is calculated by averaging successive values of the logarithm of the change variable over 30 minutes. The responsiveness index is indicative of the mean/cumulative high-frequency EEG power changes with respect to time. The Viertiö-Oja et al. application teaches that other measures may be used instead of high-frequency EEG power as the first measure, such as EEG entropy or measures based on fractal spectrum analysis, Lempel-Ziv complexity, or bispectral or multispectral analyses or the Bispectral Index.

The responsiveness index of the Viertiö-Oja et al. application is designed to differentiate between natural sleep and unconsciousness induced by sedatives is based on the theory that deepening sedation tends to suppress naturally occurring arousals, while test persons in natural sleep remain relative responsive. The responsiveness index is therefore intended to provide a selective mechanism for differentiating between sedation and natural sleep. Due to the long time window (i.e., 30 minutes) used to calculate the responsiveness index, the index is sensitive only to stimuli which result in sustained changes in high-frequency EEG power and is insensitive to isolated transient stimuli, such as those occurring during care procedures.

Knowledge of a patient's analgesic state and adequacy would enable an anesthesia provider to more effectively administer the needed pharmacological agents in the precise dosage required to ensure an optimal intraoperative patient state. This optimal state will result in improved patient outcomes. None of the systems proposed to date has disclosed a system or method of which would allow such a determination.

It is therefore an objective of this invention to provide a system and method of assessing and quantifying a patient's level of analgesic state and adequacy.

SUMMARY OF THE INVENTION

The system and method of the present invention predict and measure a subject's analgesic state and analgesic adequacy. Biopotential signals are obtained from a subject through electrodes. A processor will compute a measure that is representative of the subject's sedative state and/or muscle activity. A metric representative of such measures is then determined. The metrics are combined into an index representative of the subject's analgesic state and analgesic adequacy.

BRIEF DESCRIPTION OF THE DRAWINGS

For a fuller understanding of the nature and objects of the present invention, reference should be made to the following detailed description which should be read in conjunction with the accompanying drawings in which corresponding reference numerals refer to corresponding parts throughout the several views:

FIG. 2 illustrates the 95% confidence intervals (CI) for: (A) Standard Deviation (SD) of BIS, (B) SD of EMG, and (C) Composite Variability Index (CVI) vs. Time (in minutes) centered relative to the time of the somatic event.

FIG. 4 illustrates the 95% confidence intervals for: (A) SD of BIS, (B) SD of EMG, and (C) Composite Variability Index (CVI) estimated over the maintenance period vs. quintile of Pain Score (from least to greatest pain).

DETAILED DESCRIPTION OF THE PREFERRED EMBODIMENTS

The present invention uses changes in the intrinsic variability of a measure of a patient's consciousness during surgery to assess the patient's analgesic state and adequacy. Due to the stochastic nature of the underlying electroencephalogram (EEG), an EEG-based consciousness measure will exhibit a basal level of variability. This variability may be quantified with common variability measures, such as the standard deviation.

A perturbation applied to the patient, such as a surgical stimulus, cutting with a scalpel or tugging on muscle tissue or internal organs will result in an increase in the basal variability of the consciousness measure and therefore a concomitant increase in the variability measure used to quantify the consciousness measure variability.

This behavior appears at all levels of consciousness, not only during surgery. A sleeping subject, while not under the influence of anesthetic pharmacological agents, still has a reduced level of consciousness. Such a patient may be aroused by noise, shaking, bright lights, etc. and such an arousal will be reflected as an increase in the level of variability of their consciousness measure. A surgical patient is generally not aroused by noise or shaking, but may be aroused by a painful stimulation. If the surgical patient is administered a dose of an analgesic agent such as an opioid drug whose effect is sufficient to block the perception of the painful stimulus, the patient will not be aroused. In both cases, the patient's level of consciousness is unchanged, but her level of analgesic adequacy differs markedly and this difference is reflected in the variability of the patient's consciousness measure. When a patient has an analgesic state adequate to block the perception of painful stimuli, the intrinsic variability of their consciousness measure decreases and this decrease may be quantified by a variability metric applied to the consciousness measure.

Muscle electrical activity may be recorded from surface, needle or implanted electrodes. Such electromyographic (EMG) signals also exhibit basal levels of muscle tone or activity, which may be quantified by variability metrics. The basal level of muscle tone is reflective of the underlying level of muscle activity. Similar to a consciousness measure, the underlying variability in muscle activity can be quantified using a variability measure. Movement results in an increase in muscle activity and thus in the variability measure. Increases in the general level of perceived pain also result in an increase in the basal level of muscle activity and thus in the variability metric used to quantify EMG variability.

The current invention seeks to quantify the adequacy of the analgesic state by creating a composite index combining metrics of the variability of a consciousness metric and an EMG metric.

Figure 1:
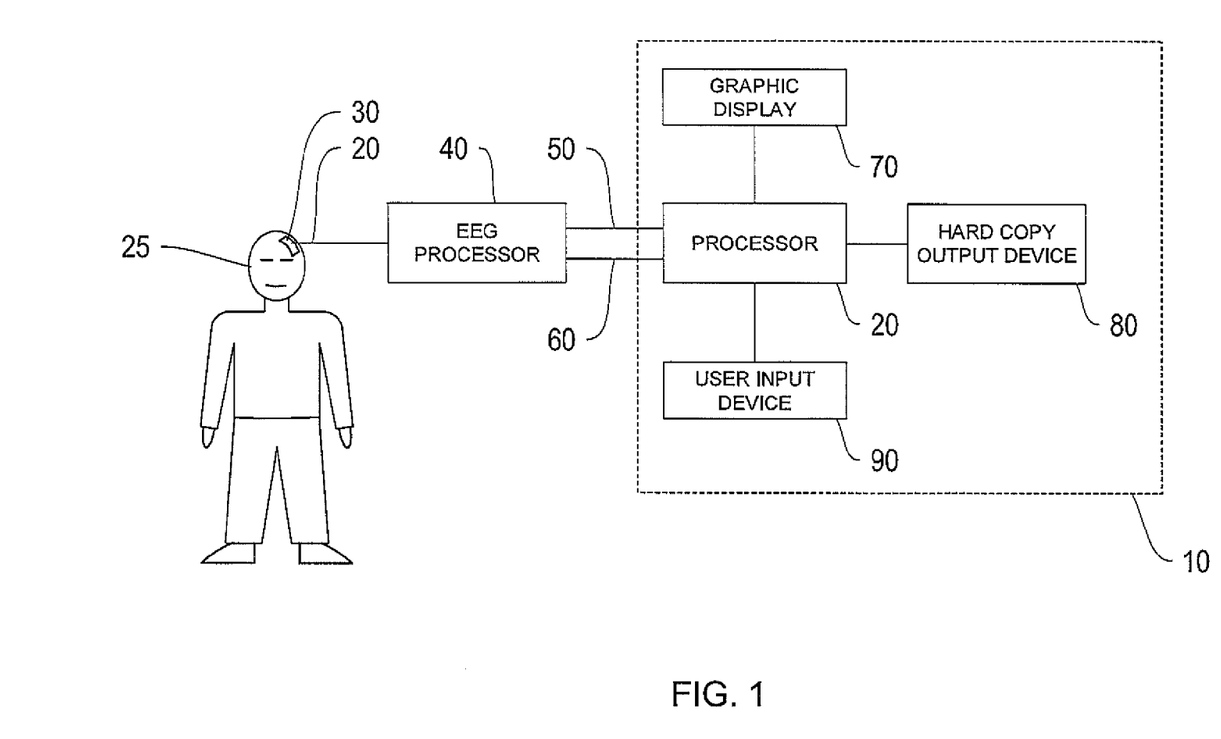
FIG. 1 shows a block diagram of an analgesic state and adequacy monitoring system constructed according to the present invention.

Referring to FIG. 1, the apparatus of the present invention includes an EEG data acquisition apparatus which provides an input signal over cable 20 to an EEG processing system 40. Said EEG processing system 40 in turn provides an input signal 50 to an analgesic state and adequacy monitoring system 10. The input signal 20 may be, for example, an EEG signal generated in known fashion by one or more EEG electrodes 30, or alternatively, by an amplifier or other known EEG processing components. The EEG leads are connected to a patient's head 25 by a set of one or more surface electrodes 30 which in a preferred embodiment are part of a BIS Quattro® Sensor (Aspect Medical Systems, Norwood, Mass.) is preferred. The EEG signals are detected by the electrodes 30 and transmitted over a cable 20 to the EEG processing system 40. The input signal 20 generated by one or more EEG electrodes 30 may be applied to any device used to process EEG signals 40 (e.g., such as a Bispectral Index generator of the type disclosed in the above-referenced U.S. Pat. No. 5,458,117). The EEG processing device 40 generates a first output signal 50 which is representative of the cerebral activity of the patient. In the preferred embodiment, the output signal 50 is representative of the patient's sedative or hypnotic state. The EEG processing device 40 generates a second output signal 60 which is representative of the electromyographic (EMG) activity of the patient. In the preferred embodiment, the second output signal 60 is representative of the level of muscle activity or tone in the muscles in the region immediately beneath the electrodes 30.

Monitoring system 10 receives the first output signal 50 representative of cerebral activity of a patient and the second output signal 60 representative of the EMG activity of the patient and computes from the two signals an index representative of the analgesic adequacy and analgesic state of the patient. This index is displayed on the graphics display 70 which is connected to the processor 20. Printed output of the index is also available on the hard copy output device 80 which is connected to the processor 20. The operator interacts with the acquisition and analysis components of the system by means of a user input device 90 with feedback on the graphics display 70.

In the preferred embodiment, first output signal 50 which is representative of the cerebral activity of the patient is the Bispectral Index® (BIS®), as generated by the product line of level of consciousness monitors manufactured by Aspect Medical Systems, Norwood, Mass., such as the A2000 monitor, the BIS Vista monitor, or the BISx module used in conjunction with a third-party patient monitoring system. In alternate embodiments, the first output signal 50 may be other measures of consciousness or anesthetic depth such as one of the entropy measures (e.g., SE and RE) generated by the line of Entropy Monitors and Modules manufactured by GE Healthcare (Finland), the PSI measure generated by the SEDLine Monitor (Hospira Inc., Lake Forest, Ill.), the AEP Index generated by the AEP Monitor (Danmeter, Odense, Denmark), the AEP Index geeraed by the AEPEX system (Medical Device Management Ltd, Braintree, UK), the SNAP Index generated by the SNAP line of monitors (Everest Biomedical Instruments, Chesterfield, Mo.) and the Narcotrend generated by the Narcotrend monitors (Schiller A G, Baar, Switzerland). Also in the preferred embodiment, the second output signal 60 is the EMG measure generated by the line of Aspect Medical Systems level of consciousness monitors. The EMG variable as computed by these monitors is the average power in the 70-110 Hz frequency band and quantifies the level of muscle activity or muscle tone. It should be obvious that in alternate embodiments other metrics or metrics calculated from other related frequency bands may be used to quantify the level of muscle activity or muscle tone, such as average power, RMS power, peak power and other measures commonly used in the art to quantify the energy in a signal or at a single frequency or in a frequency band.

Turning now to the method of the invention as implemented by the processor 20, the first and second output signals 50, 60 received by processor 20 are preferably digital, composed of consecutive regularly-spaced discrete samples. The signals 50, 60 are represented as the two time series of consecutive values $CerebralActivity_i$ and $EMG_i$, respectively. The subscript "i" represents the point in time corresponding to each value of the time series. These two time series are time-synchronized, so that $CerebralActivity_i$ and $EMG_i$ therefore correspond to the values of same instant in time.

These two time series are divided into sets of sequential samples, known as "epochs", a technique commonly performed in the art. The invention preferably uses a 15 second sampling interval and an epoch length of 60 seconds; each epoch therefore consists of 5-samples. It should of course be realized that other sampling rates and epoch lengths may be used. The epochs overlap, so that each time the new samples $CerebralActivity_i$ and $EMG_i$ become available (where the subscript i represents the most recent sample), the new epoch overlaps the previous epoch by 80%.

For each epoch of data, the processor 20 derives a measure of variability from the time series $CerebralActivity_i$ and $EMG_i$. In the preferred embodiment, the standard deviation is utilized as the measure of variability. However, it should be realized that other variability metrics may be used, such as confidence intervals, standard errors, zero-crossing counts (number of times the time series transitions from greater than to less than some threshold, often the mean value of the samples in the epoch), the location or value of a specific percentile, the number or proportion of values inside a specific range or set of percentiles or above or below a specific percentile, the mean or median of the difference between each sample in the epoch and the minimum or maximum value in the epoch or some other time period covering multiple epochs or a fraction of an epoch, or other measures of statistical variability known in the art.

The variability of the time series $CerebralActivity$, $\sigma_{CerebralActivity}$, is calculated using the commonly-known form of the sample standard deviation;

$$\sigma_{CerebralActivity} = \sqrt{\frac{\sum_{i=1}^{n}(CerebralActivity_{n-i} - \overline{CerebralActivity})^2}{n-1}}$$

$$\overline{CerebralActivity} = \frac{\sum_{i=1}^{n} CerebralActivity_{n-i}}{n}$$

Similarly, the variability of the time series EMG, the standard deviation of EMG ($\sigma_{EMG}$), is calculated as;

$$\sigma_{EMG} = \sqrt{\frac{\sum_{i=1}^{n}(EMG_{n-i} - \overline{EMG})^2}{n-1}}$$

$$\overline{EMG} = \frac{\sum_{i=1}^{n} EMG_{n-i}}{n}$$

In these calculations, n is the number of samples in an epoch. In the preferred embodiment, the measure of cerebral activity is BIS (that is, $CerebralActivity_i = BIS_i$) and therefore $\sigma_{CerebralActivity}$ is referred to as the standard deviation of BIS ($\sigma_{BIS}$). Both of the variability metrics are calculated for each epoch, and include all the data within that epoch.

It is desirable to combine the two variability metrics into a single-valued index which is correlated with analgesic state and analgesic adequacy. This has the advantage of providing a single number to the clinician as well. In addition, the single-valued index will be a more stable estimate than either of the variability metrics and will be more accurate. Like all statistical estimators, the two variability metrics have an information component correlated with analgesic state and analgesic adequacy as well as a random error component. Because their respective information components are only partially correlated, the combination of the two will contain more information than either of the components. In contrast, the error components are at least partially random with respect to each other and the combination of the two variability metrics will result in a smaller random error than either of the two components. For this reason, the combination of the two variability metrics into a single index results in a higher level of information and a lower level of random noise than either of the variability metrics alone.

The two variability metrics are combined in a linear combination. In order to derive the coefficients of the combination, a database of EEG and EMG data along with simultaneous data regarding the patient's somatic state was used. The particular form of linear combination is a logistic equation. A logistic regression was used to derive the coefficients using the variability metrics as independent variables and the presence or absence of a somatic response as the dependent variable. Variability metrics calculated from data recorded from patients immediately before the patient exhibited a somatic response of the type associated with inadequate analgesia and pain (movement, grimacing and eye opening) were associated with the presence of a somatic response, and variability metrics calculated from data 3 minutes prior to the somatic response were associated with the absence of a somatic response.

Data was collected from a multi-center, IRB-approved trial that was part of the FDA approval process for BIS (Gan T J, Glass P S A, Windsor A, et al. Bispectral Index Monitoring Allows Faster Emergence and Improved Recovery from Propofol, Alfentanil, and Nitrous Oxide Anesthesia. Anesthesiology 1997; 87 (4):808-15). Patients (n=353) undergoing elective general surgery were given propofol and alfentanil infusions with 50% $N_2O$ in $O_2$. Electrodes were placed on the patients' foreheads and temples using the BIS Sensor® as recommended by the manufacturer (Aspect Medical Systems Inc.). EEG and EMG (defined as the power in the 70-110 Hz frequency band of the EEG) were acquired by a data acquisition system consisting of amplifiers, various high pass, low pass and band-pass filters and an analog-to-digital converter which digitized the EEG and EMG signals and recorded them continuously on a computer for off-line analysis. Somatic responses (i.e., movement, grimacing and eye opening) were logged. The recorded EEG, EMG and logged somatic response data were combined to form the study database. BIS (revision 4.1) was calculated off-line from the recorded EEG. The database was scanned to select responses preceded by at least 10 minutes of no response. For development and analysis, the observation 3 minutes prior to a response was defined as Baseline (B) and the observation immediately prior to response was defined as Pre-Response (PR). The study database contained one hundred identified somatic responses.

In order to facilitate development and testing from the same data set, the study database was divided equally into development (Learning) and evaluation (Test) sets. The Learning Set was used to identify those metrics that changed between B and PR periods and are therefore associated with somatic responses. These metrics were combined into a logistic equation and the Learning Set was used to calculate the set of coefficients that provided the best fit with the somatic response data in the Learning Set. The logistic regression equation using the computed coefficients is the composite variability metric (CVM) Index. The Test Set was used to prospectively evaluate the CVM Index derived from the significant metrics. The learn/test methodology helps to avoid model over-fitting that might occur if the features were identified on the entire data set.

Using the learning set, those metrics that changed significantly from B to PR were identified, and logistic regression was used to create a composite measurement that would predict somatic response. The logistic regression's prediction of probability of response (0 to 1) was scaled from 0 to 100. The set of evaluated metrics were the average (mean) and standard deviations of both EMG ($\sigma_{EMG}$) and BIS (revision 4.1) ($\sigma_{BIS}$). These were calculated at 15 second intervals from the current epoch (data within the prior minute).

Figure 2A:
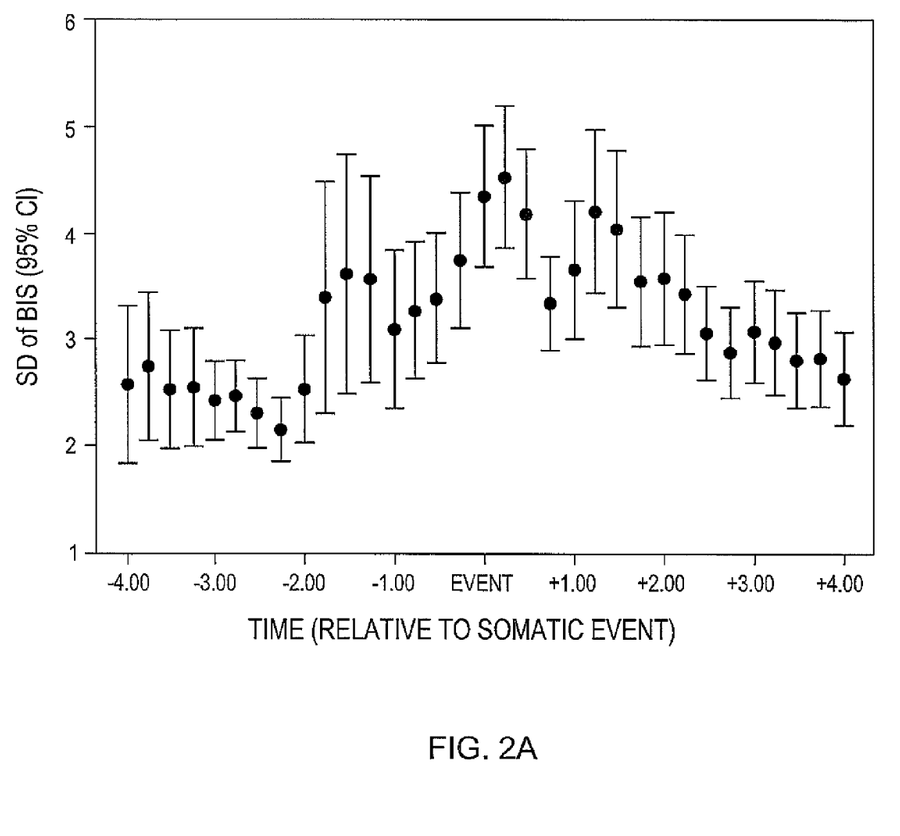
Figure 2B:
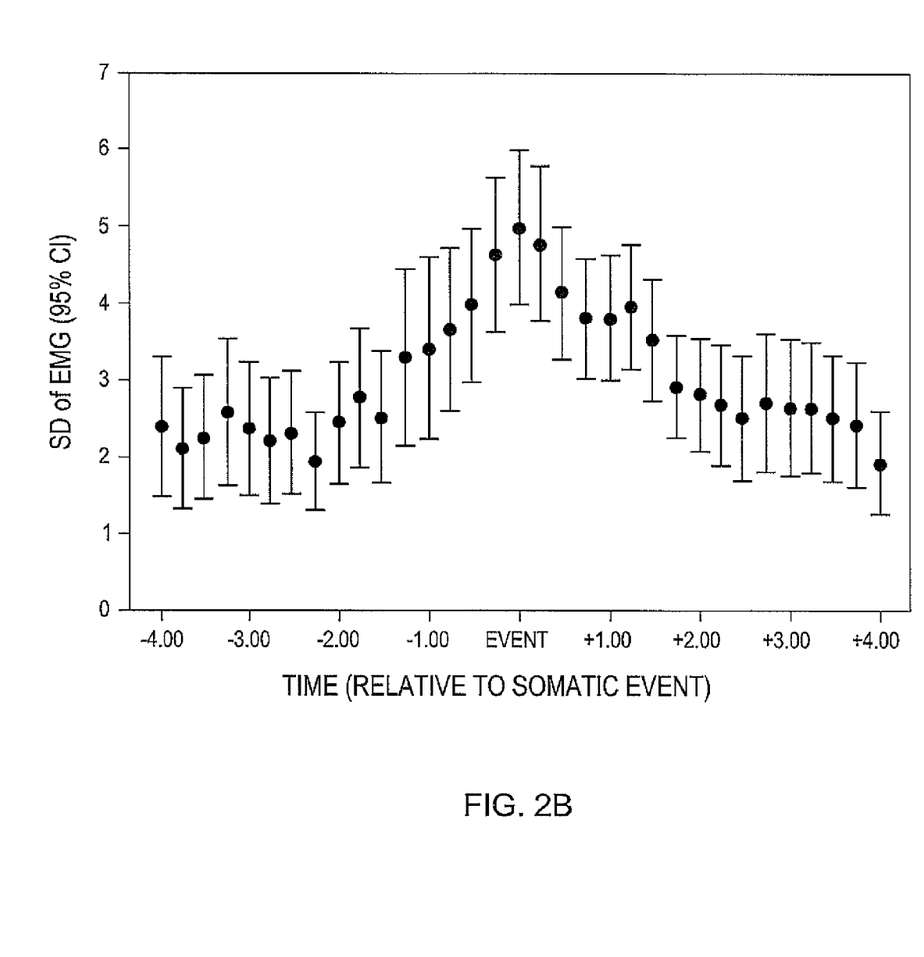
Figure 2C:
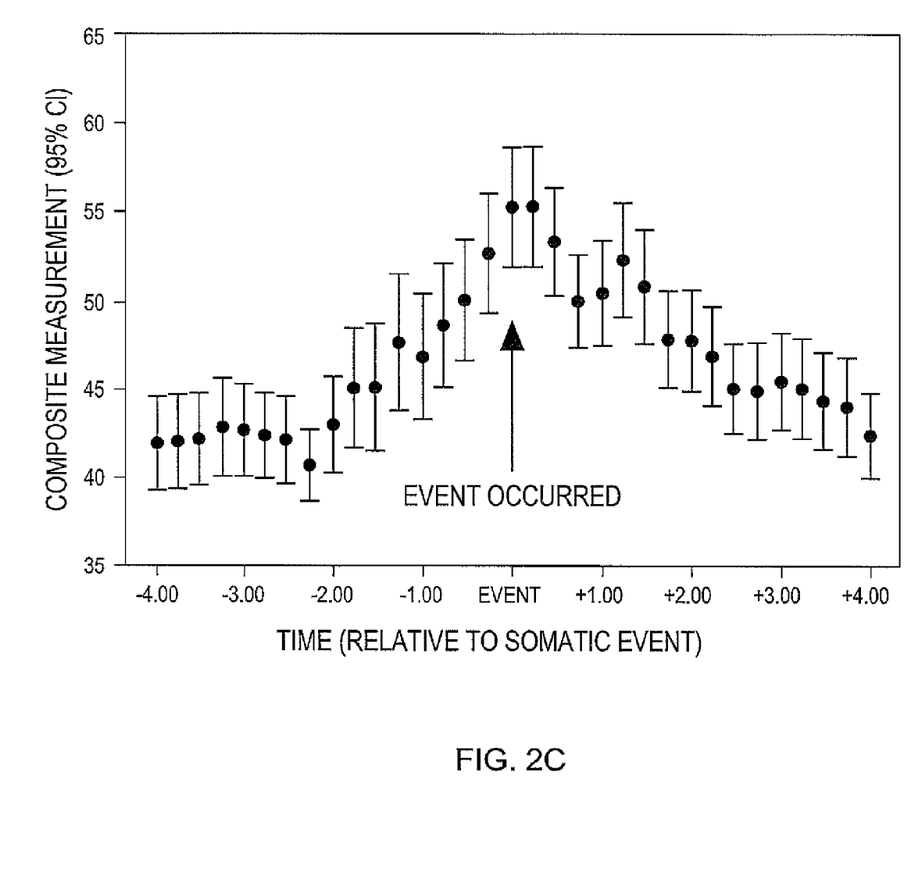

Analysis of the Learning Set identified that average EMG, standard deviations (SD) of EMG, SD of BIS, but not average BIS, increased significantly between Baseline and Pre-Response periods (FIG. 2). The Composite Variability Metric Index (CVM) was derived from the model generated by logistic regression to predict Baseline vs. Pre-Response using the previously identified features as candidate variables. The logistic regression selected the standard deviations of EMG ($\sigma_{EMG}$) and BIS ($\sigma_{BIS}$) as the most statistically significant variables when combined to form the composite measurement.

The CVM is calculated as $$CVM=100(1+e^{(\alpha*\sigma EMG+\beta*\sigma BIS+\gamma)})^{-1}$$

where $\alpha=-0.115$, $\beta=-0.153$ and $\gamma=0.937$. The coefficients $\alpha$, $\beta$ and $\gamma$ are computed using the logistic regression applied to the Learning Set.

While the preferred embodiment uses an index in the form of a logistic equation, other forms of equations may be alternately used.

All of the individual metrics as well as the CVM Index were prospectively evaluated using the Test Set, yielding results similar to those obtained in the Learning Set (Table 1). This analysis examined the predictive capacity of the CVM Index, and is based on the finding that the variability of EMG and BIS as well as EMG power increase before somatic responses during surgery.

The average trend (with 95% CI) of the SD of EMG, the SD of BIS, and the CVM Index is shown in FIG. 2. The average EMG and variability metrics (SD) of both EMG and BIS increased over the 3 minutes preceding somatic responses to surgical stimulation (i.e., movement, grimacing, or eye opening) during the anesthesia maintenance phase of general, elective surgery in patients receiving propofol/N$_2$O/alfentanil anesthesia. The CVM Index was highly correlated with the subsequent somatic response. These metrics, and their combination (the CVM Index), appear to be clinically useful indicators of periods of inadequate analgesia.

The SD of BIS ($\sigma_{BIS}$) and the SD of EMG ($\sigma_{EMG}$) are by themselves highly significant predictors of analgesic state and adequacy. In an alternate embodiment, the SD of BIS ($\sigma_{BIS}$) may be used by itself in a logistic equation to form an alternate CVM Index. In this embodiment, an alternate CVM Index (CVM$_{SDBIS}$) is calculated as $$CVM_{SDEMG}=100(1+e^{(\lambda*\sigma EMG+\nu)})^{-1}$$

where the coefficients $\kappa$ and $\epsilon$ are computed using the logistic regression applied to the Learning Set.

In another alternate embodiment, the SD of EMG ($\sigma_{EMG}$) may be used by itself in a logistic equation to form another alternate CVM Index. In this embodiment, an alternate CVM Index (CVM$_{SDEMG}$) is calculated as $$CVM_{SDEMG}=100(1+e^{(\lambda*\sigma EMG+\nu)})^{-1}$$

where the coefficients $\lambda$ and $\nu$ are computed using the logistic regression applied to the Learning Set.

The preferred embodiment, however, uses the combination of both of these metrics in a single CVM Index in order to obtain a higher level of information and a lower level of random noise than either of these two variability metrics used alone, resulting in a CVM Index with increased performance.

TABLE 1

Group Statistics of the various components of the CVM Index

| Variables estimated over 1 minute | Retrospective Development (Learning Set) n = 50 | | Prospective Evaluation (Test Set) n = 50 | |
|---|---|---|---|---|
| | Baseline | Pre-Response | Baseline | Pre-Response |
| Average BIS | 62.88 ± 15.95 | 62.41 ± 11.51 | 58.97 ± 15.70 | 60.64 ± 10.39 |
| Standard Deviation of BIS | 2.59 ± 2.17 | 3.89 ± 3.19* | 2.26 ± 1.48 | 4.83 ± 3.42*** |
| Average EMG (dB) | 35.42 ± 9.11 | 38.96 ± 8.36* | 32.58 ± 7.18 | 35.91 ± 6.97* |
| Standard Deviation of EMG (dB) | 2.64 ± 4.46 | 5.72 ± 5.62** | 2.08 ± 4.43 | 4.14 ± 4.21* |
| Composite Variability Metric (CVM Index) | 43.96 ± 13.93 | 55.16 ± 17.51*** | 41.15 ± 12.68 | 55.38 ± 16.80*** |

*p <0.05,
**p = 0.002,
***p <0.001 compared to baseline

In order to reduce the variation of the trended (time series) of the CVM Index, the change from sample to sample, it may be desirable to smooth the CVM Index. This may be accomplished by averaging some number of the most recent CVM Index values, with larger number of values being averaged together to provide a smoother and slower response, or fewer number of values being averaged together to provide a more variable and faster response. Such averaging may be equally weighted or weighted in a manner in which the influence of each CVM Index value in the average varies depending upon some weighting function. An example of such a weighting function is an inverse age function, in which the individual CVM Index values are weighted (multiplied) by the inverse of there age. This technique has the effect of weighting the most recent CVM Index values more strongly than older ones. In the preferred embodiment, smoothing is not applied, since the temporal averaging inherent in the calculation of BIS and EMG provides adequate smoothing.

It may also be desirable to increase the reliability of the CVM Index by excluding BIS and EMG values from the CVM Index calculation when these values are computed during various EEG states in which the variability of BIS and EMG are not reflective of analgesic state and adequacy. For example, EEG suppression is a state occurring during very deep sedative states in which the EEG activity becomes partly or completely isoelectric. The variability of BIS and the EMG during complete or partial EEG suppression is not reflective of a patient's analgesic state and adequacy, and the preferred embodiment of the invention does not calculate a value during this state. The consciousness monitors manufactured by Aspect Medical Systems generate a variable called Suppression Ratio (SR) which quantifies the degree to which the EEG waveform is suppressed. The preferred embodiment of the invention does not calculate a value for the CVM Index when the value of SR rises above a threshold, preferably 40.

A further analysis of the CVM Index was conducted to prospectively evaluate the ability of the intraoperative variability of the CVM Index as well as the BIS and EMG trends to predict the severity of postoperative pain. Following IRB approval and written informed consent, consecutive patients greater than 16 years of age who were undergoing non-cardiac surgery under general anesthesia were enrolled in a study initially focused on the impact of BIS monitoring on awareness [Ekman, et. al, Reduction in the Incidence of Awareness Using BIS Monitoring. Acta Anaesthesiologica Scandinavica 2004; 48(1):20-6]. The data recorded included age, gender, body mass index (BMI), type of surgery (classified as intra-abdominal, orthopedic, general, ENT, or other), ASA Physical Status, and anesthetic duration. Continuous BIS and EMG values were recorded as sequential 1-minute average values. Pain was self-reported 1 hour postoperatively using a 100 mm visual-analog scale, in which 0 represented no pain at all and 100 the worst pain possible. The pain scores were later reclassified using two methodologies; a median split into 2 rank-ordered groups of equal numbers of Less or More Pain and a quintile split into 5 rank-ordered groups of equal numbers, ranked from the Least to the Most Pain. Average EMG and the standard deviation (SD) of EMG and BIS were calculated over the maintenance period (defined as intubation to skin closure) to assess intraoperative variability.

Intraoperative, postoperative and mortality data were available for 2,248 patients. Patients with postoperative pain greater than the median value had larger BMI, younger age, longer case duration, greater average EMG and greater average variability (SD) of both EMG and BIS (Table 2). The multivariate ANOVA model that best explained the variance in pain score contained all the significant univariate variables in Table 2.

TABLE 2

Parameter Statistics for each Pain Group (mean ± standard deviation)

| Parameter | Lesser Pain Group | Greater Pain Group | P-value |
|---|---|---|---|
| Pain Score | 6.47 ± 8.67 | 51.28 ± 16.70 | <0.001 |
| SD of BIS | 9.08 ± 3.26 | 9.41 ± 3.44 | 0.020 |
| Average EMG (dB) | 30.26 ± 2.29 | 30.77 ± 2.45 | <0.001 |
| SD EMG (dB) | 3.97 ± 2.33 | 4.68 ± 2.51 | <0.001 |
| Age (years) | 49.4 ± 17.4 | 47.2 ± 16.6 | 0.002 |
| BMI (kg/m$^2$) | 25.33 ± 4.23 | 26.02 ± 4.77 | <0.001 |
| Case Duration (min) | 102.39 ± 56.39 | 108.57 ± 53.37 | 0.008 |

Figure 3:
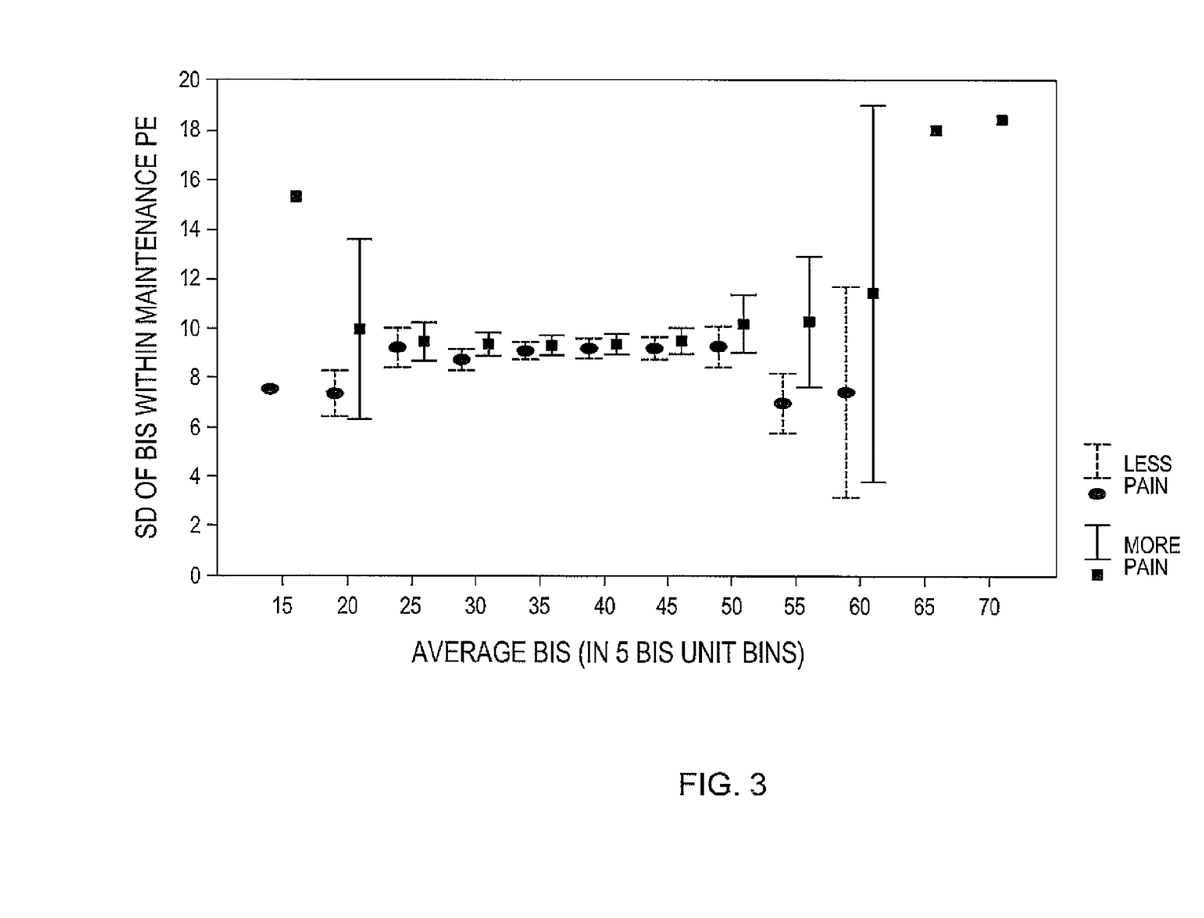
FIG. 3 illustrates the 95% confidence intervals for the SD of BIS within the maintenance phase per average BIS within the maintenance phase (in 5 BIS unit bins) per Pain Group (More vs. Less Pain).

In order to evaluate the relationship between the BIS range and the variability of BIS, the average and SD of all BIS values within the maintenance period were calculated for each patient. This data is shown in FIG. 3, with the individual patient values grouped by average BIS values. Patients with pain greater than the median at 1 hour postoperatively had greater variability of BIS at each BIS level (p=0.013).

Figure 4A:
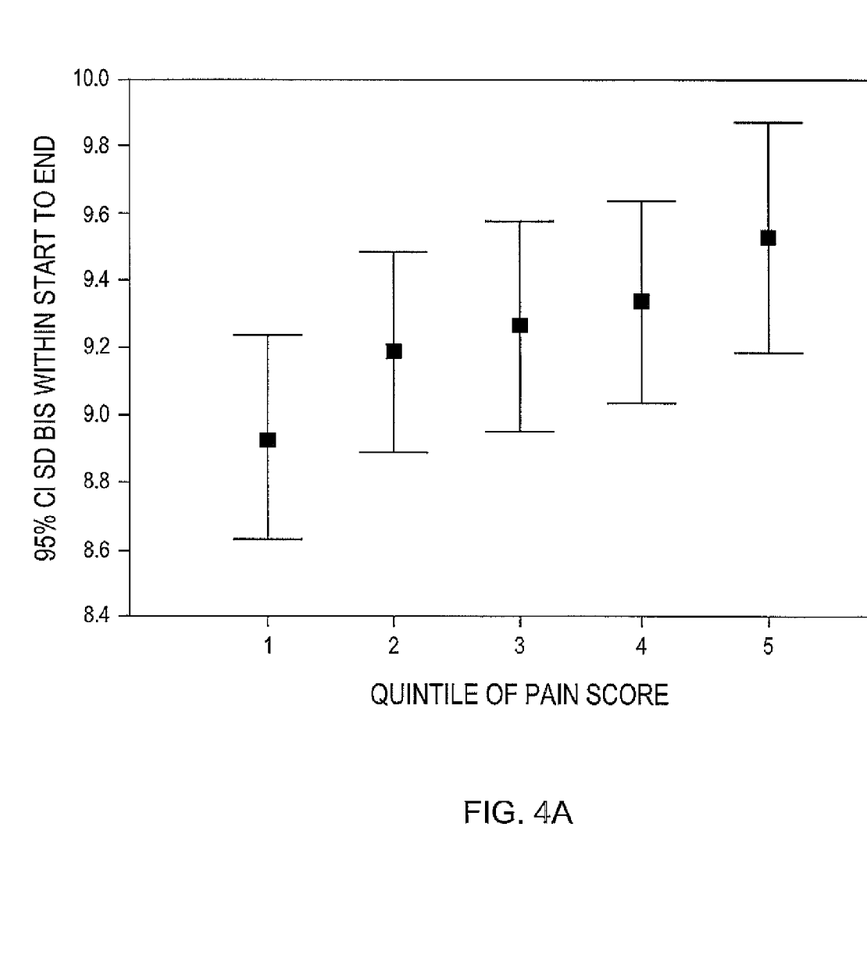
Figure 4B:
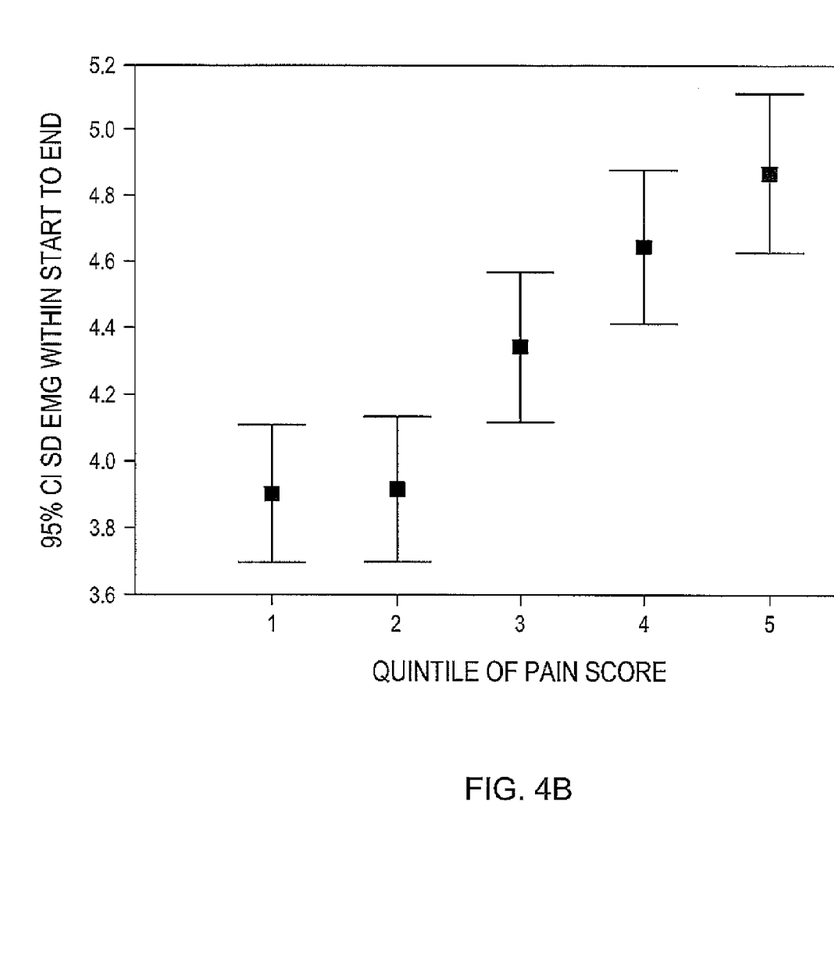
Figure 4C:
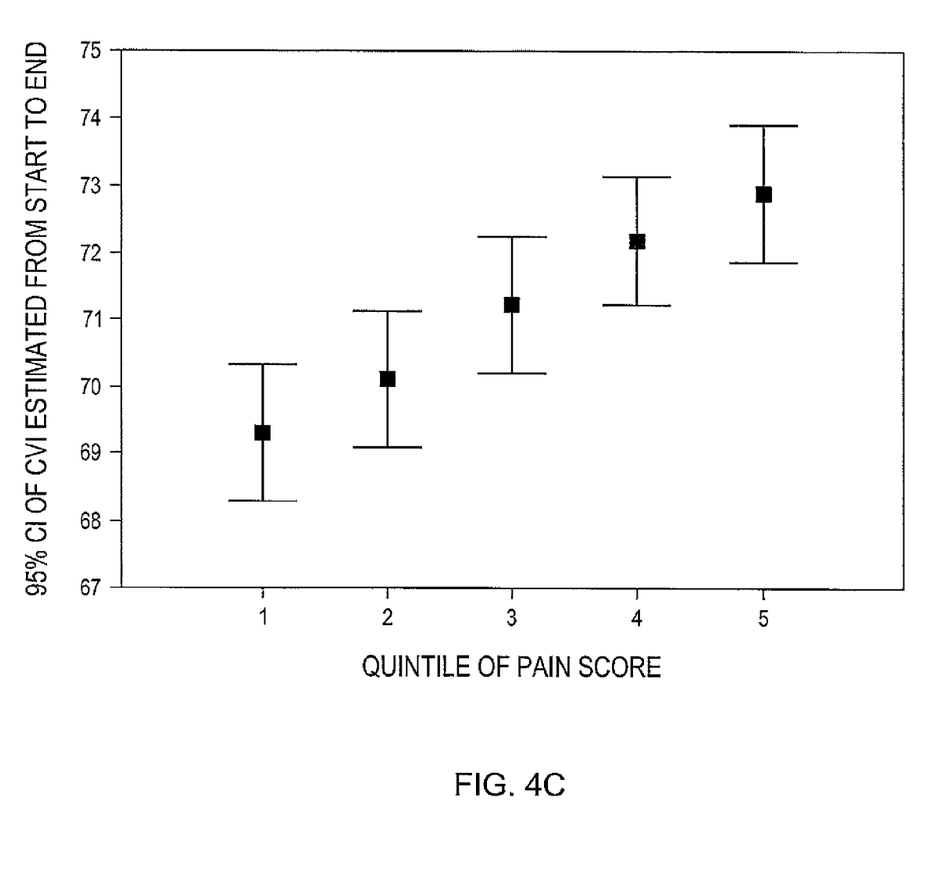

The analysis of the pain scores ranked by quintiles is shown in FIG. 4. Graph A in FIG. 4 shows a rank-ordered increase in the SD of BIS with increased pain score. The increase of SD of BIS is consistent across the range of pain scores. Graph B in FIG. 4 shows the relationship between the SD of EMG and pain score. While there is essentially no difference in the SD of EMG at the two lowest pain scores (1 and 2), there is a rapid rank-ordered increase with pain scores 3-5. Graph C in FIG. 4 shows the relationship of the CVM Index to postoperative the pain score. The combination of the SD of both BIS and EMG in the CVM Index results in a consistent rank-ordered increase across pain scores. This behavior is a significant improvement over the SD of EMG alone, affording differentiation between pain scores in the lower pain levels. The CVM Index also provides a rank-ordered assessment and prediction of post-operative pain with less variability (a smaller confidence interval, CI) than that of the SD of BIS alone.

A further embodiment of the invention is the use of the CVM Index to improve postoperative patient outcome. This may be accomplished by using the CVM Index to guide the administration of analgesic agents. During the maintenance phase of anesthesia (after induction and prior to emergence), the dosage of analgesic agents administered to the patient is titrated with the goal of maintaining the CVM Index at low values. Such titration must, of course, be consistent with the clinician's judgment in order to avoid excessive analgesic doses. For example, the anesthesia provider may observe the CVM Index, monitoring it for increases above the level observed during a known pain-free period, such as early in the surgery before the first incision. The anesthesia provider may also monitor the CVM Index for increases above the level observed during periods of time in which there is an absence of surgical stimulation. Increases that are sudden or sustained are particularly meaningful and may be associated with a sudden painful stimulus while the patient's analgesic state is inadequate.

While the foregoing invention has been described with references to its preferred embodiments, various alterations and modifications are likely to occur to those skilled in the art. All such alterations and modifications are intended to fall within the scope of the appended claims.

What is claimed is:

1. A system for assessing a subject's analgesic state and adequacy comprising:
   a plurality of electrodes for obtaining biopotential signals from said subject at intervals over a period of time; and
   a processor configured for:
      computing from said biopotential signals a first measure representative of the subject's sedative state;
      calculating a first metric representative of variability of said first measure;
      computing from said biopotential signals a second measure representative of the subject's muscle activity;
      calculating a second metric representative of variability of said second measure; and
      calculating from said first and second metrics an index representative of the subject's analgesic state and analgesic adequacy.

2. The system for assessing a subject's analgesic state and adequacy of claim 1, wherein said processor is further configured for assigning weights to at least one of said first and second metrics, and calculating an index from at least one of said first and second metrics based on said weights.

3. The system for assessing a subject's analgesic state and adequacy of claim 1, wherein calculating the index comprises combining said first metric and said second metric to calculate the index representative of said subject's analgesic state and analgesic adequacy.

4. The system for assessing a subject's analgesic state and adequacy of claim 3, wherein said processor is further configured for assigning weights to said first metric and said second metric, and combining said first metric and said second metric into the index based on said weights.

5. The system for assessing a subject's analgesic state and adequacy of claim 1, wherein said processor is further configured for time synchronizing said first measure and said second measure.

6. The system for assessing a subject's analgesic state and adequacy of claim 3, wherein combining the first and second metrics includes combining the first and second metrics in a linear combination.

7. The system for assessing a subject's analgesic state and adequacy of claim 6, wherein the linear combination is a logistic equation.

8. The system for assessing a subject's analgesic state and adequacy of claim 1, wherein the first metric representative of variability is based, at least in part, on standard deviation of the first measure, and the second metric representative of variability is based, at least in part, on standard deviation of the second measure.

9. The system for assessing a subject's analgesic state and adequacy of claim 1, wherein the processor is further configured for smoothing the index by averaging a plurality of index values.

10. The system for assessing a subject's analgesic state and adequacy of claim 1 further comprising a display, connected to the processor, for displaying the index representative of the subject's analgesic state and analgesic adequacy.

11. The system for assessing a subject's analgesic state and adequacy of claim 1, wherein the processor calculates a first alternate index representative of the subject's analgesic state and analgesic adequacy from the first metric representative of variability.

12. The system for assessing a subject's analgesic state and adequacy of claim 11, wherein the processor calculates a second alternate index representative of the subject's analgesic state and analgesic adequacy from the second metric representative of variability.

13. The system for assessing a subject's analgesic state and adequacy of claim 1, wherein the first metric representative of variability is based, at least in part, on a first confidence interval associated with the first measure, and the second metric representative of variability is based, at least in part, on a second confidence interval associated with the second measure.

14. The system for assessing a subject's analgesic state and adequacy of claim 1, wherein the first metric representative of variability is based, at least in part, on a first threshold associated with the first measure, and the second metric representative of variability is based, at least in part, on a second threshold associated with the second measure.

15. The system for assessing a subject's analgesic state and adequacy of claim 1, wherein the first metric representative of variability is based, at least in part, on a first standard error associated with the first measure, and the second metric representative of variability is based, at least in part, on a second standard error associated with the second measure.

16. The system for assessing a subject's analgesic state and adequacy of claim 1, wherein the first metric representative of variability is based, at least in part, on a first range associated with the first measure, and the second metric representative of variability is based, at least in part, on a second range associated with the second measure.

17. The system for assessing a subject's analgesic state and adequacy of claim 1, wherein the intervals over a period of time comprise 15 second intervals.

18. The system for assessing a subject's analgesic state and adequacy of claim 1, wherein the processor is further configured for smoothing the index by assigning weights to each of a plurality of index values and by averaging the plurality of index values based at least in part on the weights.

19. The system for assessing a subject's analgesic state and adequacy of claim 1, wherein the processor is further configured for determining from which of the first and second measures to determine the index.

20. The system for assessing a subject's analgesic state and adequacy of claim 19, wherein the processor is further configured for determining from which of the first and second measures to determine the index based on the subject's EEG state.

* * * * *